United States Patent
Miettinen et al.

(10) Patent No.: US 10,874,901 B2
(45) Date of Patent: Dec. 29, 2020

(54) AUTOMATIC INFORMATION SYSTEM

(71) Applicant: Suunto Oy, Vantaa (FI)

(72) Inventors: Michael Miettinen, Tuusula (FI); Heikki Nieminen, Espoo (FI); Erik Lindman, Espoo (FI); Mikko Ahlström, Helsinki (FI)

(73) Assignee: Suunto Oy, Vantaa (FI)

( * ) Notice: Subject to any disclaimer, the term of this patent is extended or adjusted under 35 U.S.C. 154(b) by 0 days.

(21) Appl. No.: 14/945,851

(22) Filed: Nov. 19, 2015

(65) Prior Publication Data

US 2018/0099182 A1    Apr. 12, 2018

(51) Int. Cl.

| | | |
|---|---|---|
| *G01D 11/00* | (2006.01) | |
| *G06F 11/30* | (2006.01) | |
| *G06F 15/00* | (2006.01) | |
| *G21C 17/00* | (2006.01) | |
| *A63B 24/00* | (2006.01) | |
| *G06K 9/00* | (2006.01) | |
| *A61B 5/11* | (2006.01) | |
| *A61B 5/00* | (2006.01) | |
| *G04G 99/00* | (2010.01) | |

(52) U.S. Cl.
CPC ............ *A63B 24/0006* (2013.01); *A61B 5/11* (2013.01); *A61B 5/681* (2013.01); *G04G 99/006* (2013.01); *G06K 9/00342* (2013.01); *A63B 2024/0068* (2013.01); *A63B 2024/0071* (2013.01)

(58) Field of Classification Search
CPC .......... A63B 24/00067; A63B 24/0006; G04G 99/006

USPC ........................................................ 702/127
See application file for complete search history.

(56) References Cited

U.S. PATENT DOCUMENTS

| | | |
|---|---|---|
| 7,129,835 B2 | 10/2006 | Nikkola |
| 7,152,470 B2 | 12/2006 | Impio et al. |
| 7,271,774 B2 | 9/2007 | Puuri |
| 7,324,002 B2 | 1/2008 | Iso-Heiko et al. |
| 7,349,805 B2 | 3/2008 | Kaltto et al. |
| 7,379,712 B2 | 5/2008 | Saamimo |
| 7,383,081 B2 | 6/2008 | Butt et al. |
| 7,515,938 B2 | 4/2009 | Ruotsalainen et al. |
| 7,600,426 B2 | 10/2009 | Savolainnen et al. |
| 7,764,990 B2 | 7/2010 | Martikka et al. |
| 7,797,039 B2 | 9/2010 | Koivumaa et al. |
| 7,803,117 B2 | 9/2010 | Martikka et al. |
| 7,936,226 B2 | 5/2011 | Akkila |
| 8,021,306 B2 | 9/2011 | Martikka et al. |
| 8,024,023 B2 | 9/2011 | Tolvanen |
| 8,275,311 B2 | 9/2012 | Lindman |

(Continued)

FOREIGN PATENT DOCUMENTS

| | | |
|---|---|---|
| CN | 202649695 | 1/2013 |
| EP | 2189191 | 5/2010 |
| WO | 2011028383 A1 | 3/2011 |

*Primary Examiner* — Michael P Nghiem
(74) *Attorney, Agent, or Firm* — Terence P. O'Brien (57) ABSTRACT

Selecting the information displayed on a sports watch, the watch comprising an interface for receiving movement information from at least one sensor; a display; and at least two display modes, wherein at least one mode is a sport mode configured to display sport-specific data. The method according to the invention comprises detecting a sport event based on the movement information received from the at least one sensor; and selecting the sport mode according to the detected sport event.

13 Claims, 5 Drawing Sheets

(56) References Cited

U.S. PATENT DOCUMENTS

| | | |
|---|---|---|
| 8,292,820 B2 | 10/2012 | Punkka et al. |
| 8,371,745 B2 | 2/2013 | Manni |
| 8,386,009 B2 | 2/2013 | Lindberg et al. |
| 8,750,959 B2 | 6/2014 | Lindberg et al. |
| 9,339,198 B2 | 5/2016 | Lindman |
| 9,468,835 B2 | 10/2016 | Martikka et al. |
| 10,356,189 B2 * | 7/2019 | Miettinen ............... H04L 67/22 |
| 2007/0285868 A1 | 12/2007 | Lindberg et al. |
| 2008/0109158 A1 | 5/2008 | Huhtala et al. |
| 2008/0119329 A1 | 5/2008 | Punkka et al. |
| 2008/0225645 A1 * | 9/2008 | Ishihara .................. G04F 10/00 368/10 |
| 2008/0289415 A1 | 11/2008 | Savolainen et al. |
| 2008/0319330 A1 | 12/2008 | Juntunen et al. |
| 2009/0312657 A1 | 12/2009 | Martikka et al. |
| 2010/0099539 A1 * | 4/2010 | Haataja ............. A63B 24/0062 482/8 |
| 2010/0130123 A1 | 5/2010 | Lindman |
| 2010/0187074 A1 | 7/2010 | Manni |
| 2011/0128824 A1 | 6/2011 | Downey et al. |
| 2011/0161455 A1 | 6/2011 | Johnson et al. |
| 2011/0230274 A1 | 9/2011 | Lafortune et al. |
| 2011/0263993 A1 | 10/2011 | Martikka et al. |
| 2012/0015779 A1 * | 1/2012 | Powch ............... A61B 5/02055 482/9 |
| 2012/0215116 A1 | 8/2012 | Martikka et al. |
| 2012/0254212 A1 | 10/2012 | Shaw et al. |
| 2013/0063288 A1 * | 3/2013 | Bley ...................... H04L 43/04 341/87 |
| 2013/0194066 A1 * | 8/2013 | Rahman ................... G05B 1/01 340/5.51 |
| 2013/0204567 A1 | 8/2013 | Nieminen et al. |
| 2013/0311123 A1 | 11/2013 | Nieminen et al. |
| 2013/0337828 A1 | 12/2013 | Fink |
| 2014/0087685 A1 * | 3/2014 | Kellond ................... G06F 3/041 455/404.2 |
| 2014/0100788 A1 | 4/2014 | Heikkinen et al. |
| 2014/0172355 A1 | 6/2014 | Kawamoto |
| 2014/0277628 A1 | 9/2014 | Nieminen et al. |
| 2014/0282131 A1 | 9/2014 | Castro et al. |
| 2015/0071039 A1 | 3/2015 | Rahkonen et al. |
| 2015/0071280 A1 | 3/2015 | Ahola et al. |
| 2016/0150039 A1 | 5/2016 | Miettinen ............... H04L 67/22 709/204 |
| 2017/0160898 A1 * | 6/2017 | Lee ................... H04W 52/0254 |

\* cited by examiner

AUTOMATIC INFORMATION SYSTEM

CROSS-REFERENCE TO RELATED PATENT APPLICATIONS

The present application claims priority under 35 U.S.C. Section 119 from Finnish Patent Application Serial No. 20146020 filed on Nov. 20, 2014 and English Patent Application Serial No. 1420637.9 filed on Nov. 20, 2014.

FIELD OF THE INVENTION

The invention relates to wrist-top computers. In particular, the present invention relates to a method, a sports watch and a computer program for selecting the information displayed on a sports watch.

BACKGROUND

The sports watch is a small microcontroller-operated device, for example a wrist-top computer which can be used for monitoring and/or tracking sports exercises. The recorded sports exercise data may be transmitted to the Internet and shared with other users or athletes. Results are usually compared with other users. Recorded tracks may be saved and assigned as events by users, wherein the user must manually indicate a track, route, path or any kind of comparable criteria or performance information to the computer. In this context the comparable sport information is an event.

The sports watch is a relatively small device with a limited screen size. The user interface is usually operated with a few buttons that are operable during a sport exercise such as running—thus limiting the number of buttons and increasing the size of the buttons. The sports watch must be robust enough to withstand all various elements encountered during the sports exercise. The user must press buttons in order to change the display mode, thus making the operation difficult for the user.

SUMMARY OF THE INVENTION

A first aspect discloses a method for selecting the information displayed on a sports watch, the watch comprising an interface for receiving movement information from at least one sensor, a display and at least two display modes, wherein at least one mode is a sport mode configured to display sport-specific data. A sport event is detected based on the movement information received from the at least one sensor; and the sport mode is selected according to the detected sport event. In an embodiment the sports watch comprises a positioning sensor providing positioning information and a wireless communication interface for receiving wireless sensor information. The wireless communication interface may be used to transmit and receive data.

In an embodiment the interface for receiving movement information from at least one sensor is integrated into the sports watch. At least one sensor may be integrated into the sports watch, wherein the sports watch may comprise at least one sensor providing movement information. In one embodiment the method comprises receiving wireless sensor information from a wireless sensor via the wireless communication interface; comparing the wireless sensor information to predefined reference data, and when the wireless sensor information corresponds to the predefined reference data; detecting and selecting the sport event according to the result of the comparison. The wireless sensor may be purposed for a specific sport, wherein detecting a specific sport from the context of the wireless sensor enables the sports watch to select the sport mode. The predefined reference data enables detecting the correct sport mode. In one embodiment the method comprises detecting at least two wireless sensors and selecting the sport mode corresponding to the at least two wireless sensors. The combination of sensor types may enable detecting the suitable sport mode. For example a wind sensor alone is suitable for archery and sailing but the combination of wind sensor and speed sensor enables to limit the sport mode to sailing. The detection of suitable sport mode may be improved by detecting further sensors.

In one embodiment the method comprises connecting the sports watch to a database of performance reference data via the wireless communication interface; and receiving performance reference data from the database. In one embodiment the method comprises the sports watch collecting performance data comprising movement information for a predefined period, comparing the performance data to the performance reference data and storing the performance data in the memory if the collected data is detected as a sport event.

In one embodiment the method comprises the sports watch collecting performance data to a circular buffer, comparing the collected performance data to the performance reference data, wherein the performance reference data comprises a typical value range, detecting the sport event data exceeding the typical value range and storing the sport event as a special sport event.

A second aspect discloses a sports watch comprising a display having at least two display modes, wherein at least one mode is a sport mode configured to display sport-specific data; at least one processor; and at least one memory including computer program code for one or more programs, the at least one memory and the computer program code operating together with the at least one processor to cause the apparatus to perform at least the following: select the information displayed on a sports watch. According to the invention the at least one processor causes the apparatus to perform at least the following: detect a sport event based on the movement information received from the at least one sensor; and select the sport mode according to the detected sport event. The sports watch may comprise various sensor configurations, for example a positioning sensor providing positioning information, a motion sensor and a wireless communication interface for receiving wireless sensor information. The sports watch comprises an interface for receiving sensor information from various sources, for example from internal sensors integrated into the sports watch.

In one embodiment the at least one processor causes the apparatus to receive wireless sensor information from a wireless sensor via the wireless communication interface; compare the wireless sensor information to predefined reference data, and when the wireless sensor information corresponds to the predefined reference data; detect and select the sport event according to the result of the comparison.

In one embodiment the at least one processor causes the apparatus to detect at least two wireless sensors and select the sport mode corresponding to the at least two wireless sensors.

In one embodiment the at least one processor causes the sports watch to connect to a database of performance reference data via the wireless communication interface and receive performance reference data from the database.

In one embodiment the at least one processor causes the apparatus to detect the wireless communication interface being connectable to a database of performance references and to receive the performance reference data.

In one embodiment the at least one processor causes the apparatus to collect performance data comprising movement information for a predefined period, to compare the performance data to the performance reference data and to store the performance data in the memory if the collected data is detected as a sport event.

In one embodiment the at least one processor causes the apparatus to collect performance data to a circular buffer, to compare the collected performance data to the performance reference data, wherein the performance reference data comprises a typical value range, to detect the sport event data exceeding the typical value range and to store the sport event as a special sport event.

A third aspect discloses a non-transitory computer program comprising computer program code embodied on a tangible computer-readable medium, the computer program code configured to carry out the method as described hereinbefore.

The embodiments of the invention described hereinbefore may be used in any combination with each other. Several of the embodiments may be combined together to form a further embodiment of the invention. A method, an apparatus, a computer program or a computer program product to which the invention is related may comprise at least one of the embodiments of the invention described hereinbefore. It is to be understood that any of the above embodiments or modifications can be applied singly or in combination to the respective aspects to which they refer, unless they are explicitly stated as excluding alternatives.

The present invention simplifies the user interface of the sports watch, requiring fewer actions from the user and still being able to visualize interesting facts for the user.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION

Reference will now be made in detail to the embodiments of the present invention, examples of which are illustrated in the accompanying drawings.

Figure 5:
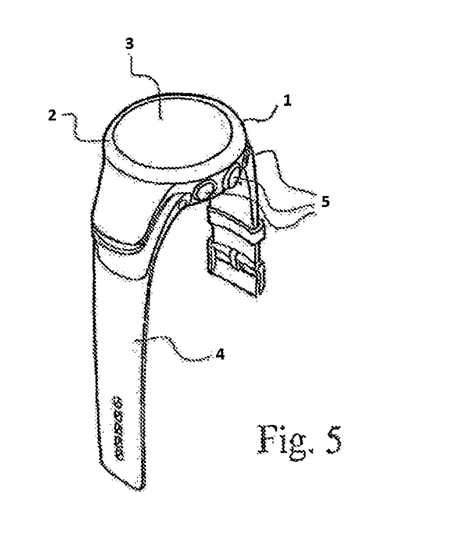
FIG. 5 is a schematic illustration of a sports watch.

FIG. 5 illustrates a schematic picture of a sports watch according to one embodiment. The sports watch 1 comprises a housing 2 carrying a display 3. The housing 2 is attached to a wristband 4. The sports watch comprises means for user interaction, such as buttons 5 in the exemplary device. In alternative preferred embodiments, other forms of inputs can also be used, such as touch screens, dials, remote transmissions, etc. The display 3 is adapted to show information to the user.

Figure 6:
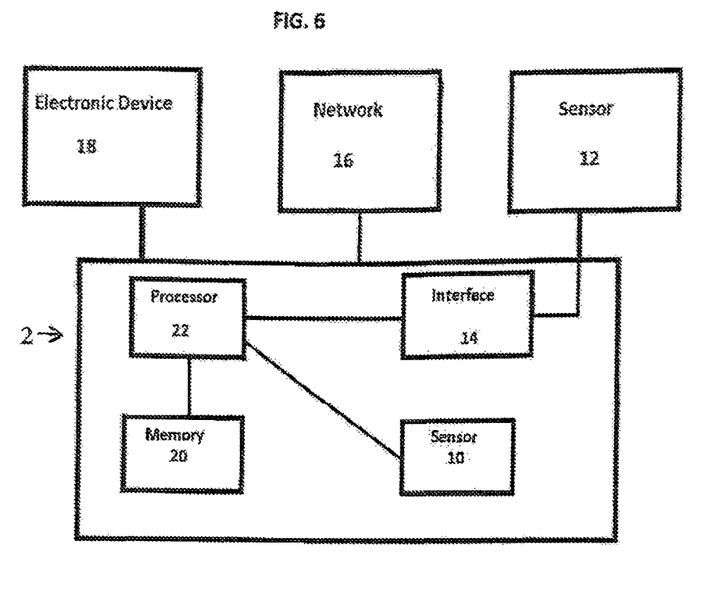
FIG. 6 is a schematic illustration of an example sports watch system.

FIG. 6 illustrates an example sports watch system. The sports watch 1 comprises sensors arranged to the housing 2 (sensor 10) or sensors that are connectable to the housing 2 wirelessly or in some embodiments by wire (sensor 12). The sensor 10 and/or 12 can be one or more of many different types of sensors, such as, for example, a positioning sensor, a compass sensor, a motion sensor, a speed sensor, an acceleration sensor, a rotational sensor, a wind sensor, a sailing sensor, a wheel speed sensor, a cadence sensor, a temperature sensor, other sensors, and/or combinations thereof. A positioning sensor provides positioning information. Examples of the positioning sensor are a compass sensor or sensors configured to acquire a position form satellite positioning systems such a GPS, GLONASS or Galileo; indoor positioning systems acquiring the information from a cell network, Wi-Fi network or from any indoor beacon system. The motion sensor is for example an inertial sensor, an accelerometer, a gyroscope sensor, a MEMS sensor or a sensor for measuring acceleration, tilt, shock, vibration, rotation, and a multiple degrees-of-freedom sensor.

The sports watch 1 comprises a wireless communication interface 14 for connecting to the sensor 12 and receiving wireless sensor information. The interface 14 may be NFC, RFID, Bluetooth, Wi-FI or a similar close perimeter communication. The wireless communication interface may also be configured to connect to an IP network 16 via a mobile data connection for receiving and transmitting data. Examples of a mobile data connection are transmission technologies such as GSM, GPRS, 3G, LTE or any other means of cellular communication. The wireless communication interface may be connectable to the IP network 16 also via a short range connection to the mobile phone and using the mobile phone's data connection entering the IP network.

The sports watch 1 may be part of a personal network 16, wherein the personal network 16 may comprise electronic devices 18 or sensors 12 connected to the sports watch 1 wirelessly or via a wired connection. The sports watch 1 may utilize the information provided by other devices as the personal network enables the sensor data to be transmitted between devices connected to the personal network. For example, electronic devices 18 can include a mobile phone or a smart phone may be connected to the sports watch 1, wherein the positioning data acquired by the mobile phone is sent to the sports watch 1. The data received by the sports watch 1 may be sent to other devices; for example, the sports watch 1 may receive heart rate data from a heart rate sensor 12 and send the heart rate data information to be displayed on the mobile phone. Examples of sensors 12 connectable to the personal network 16 are: a cadence sensor for measuring a pedaling rate, a power meter or a wheel speed sensor for a cycle; sailing sensors such as a wind speed sensor or a wind direction sensor; any suitable sensor on a motor vehicle such as a positioning sensor. Devices on the personal network may be connected by a Bluetooth, Bluetooth LE, ANT+ or any other wireless connection interface that may support a low power transmission technology.

The sports watch 1 comprises several sport modes configured for certain sports, wherein the sport mode may seek a predefined sensor configuration or display characteristics most suitable for that sport. Sport modes may be preconfigured for the sports watch 1 or the user may configure additional sport modes with a desired sensor configuration, display appearance and/or values to be calculated by the sports watch 1. One of the display modes may be a traditional watch mode, where the display shows the time and/or date.

Figure 1:
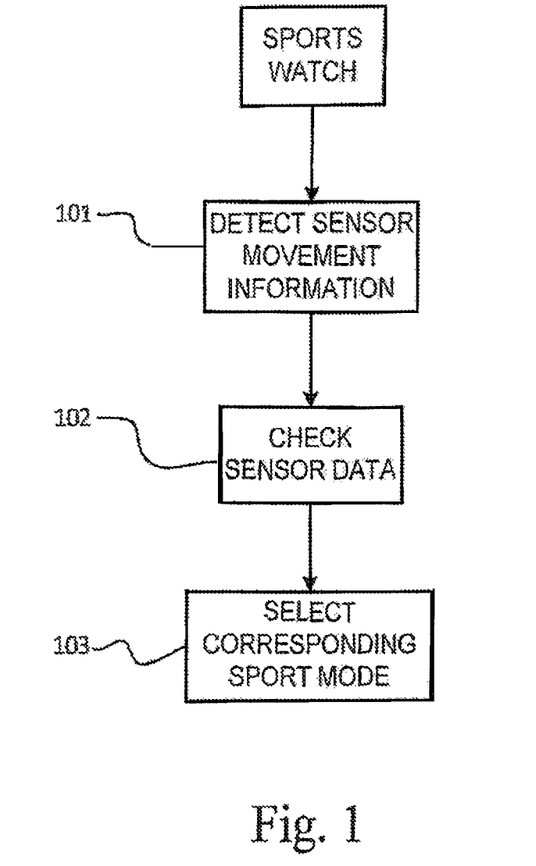
FIGS. 1-4 are flowcharts illustrating functions of embodiments according to the invention

FIG. 1 illustrates a flowchart with functions of one embodiment according to the invention. In step 101 the movement information is detected from the sensors 10 or 12. The movement may be detected from the GPS sensor, compass sensor or from the accelerometer. In this example the information received is typical for a certain sport that can be detected from the speed of moving, repeating cycles, directions—all indicating if the user is for example walking, running or cycling. Sensor data is checked in step 102 for whether additional data can be acquired—for example the low temperature enabling certain winter sports or altimeter data combined with temperature and speed indicates downhill skiing. In step 103 the sports watch 1 selects automatically the display for a correct sport mode.

Figure 2:
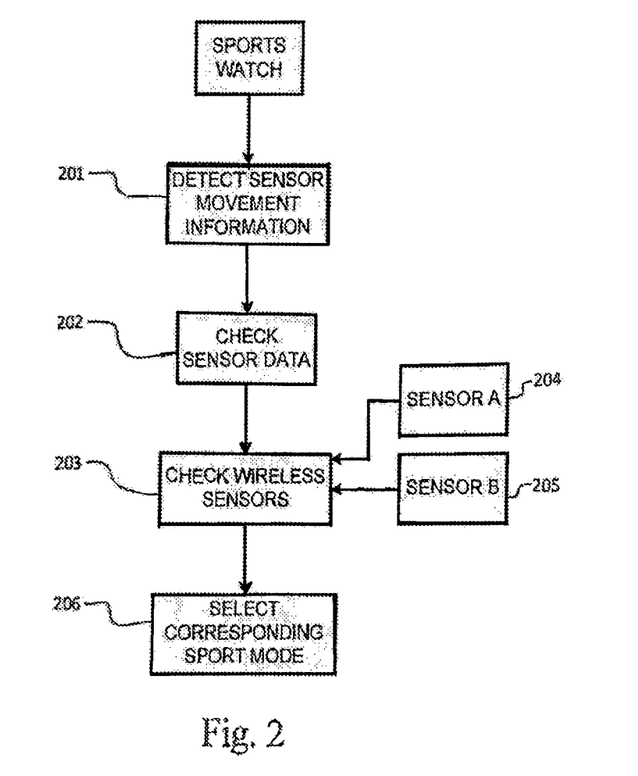

FIG. 2 illustrates a similar starting point in steps 201 and 202 as with FIG. 1, steps 101 and 102. In step 203 the sports watch 1 checks wireless sensors 12. For example by detecting a cadence sensor A in step 204 and a cycle speed sensor B in step 205, the sports watch has the information that sensors related to cycling are active, since the cadence sensor transmits data and the wheel of the bicycle is spinning In step 206 the sports watch 1 selects a correct sport mode, which in this example relates to cycling. The cycling sport mode may be a default mode predefined in the sports watch 1 or it may be modified and later installed in the sports watch 1 by the user by using a computer implemented tool provided with the sports watch 1.

Figure 3:
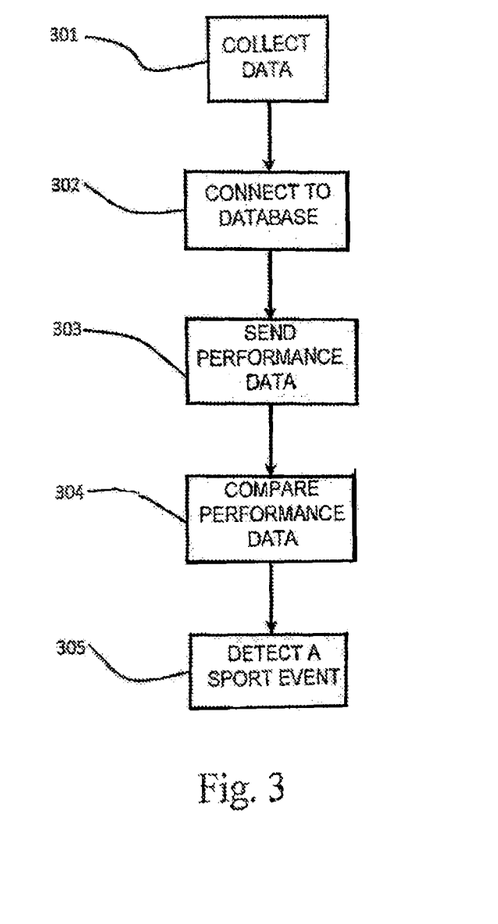

FIG. 3 illustrates a flowchart where the sports watch 1 collects data from sensors 10 and/or 12, step 301. In this example the wireless communication interface is connected to the database of performance references, step 302. The sports watch 1 sends the performance data to the server in the IP network 16 that is connected to a database of performance references, step 303. The database comprises previous sport performances from multiple users that have uploaded their sport performances to the database. Some performances have been stored as events—similar tracks or routes that many users can use and compare their results with each other. Events can be categorized according to age, gender or other suitable category. In step 304 the performance data sent by the sports watch is compared to the data of other performances. If the database comprises a matching event, it assigns the performance of the user as participating in the event automatically or prompts the user of whether the performance should be assigned as an event, step 305.

Figure 4:
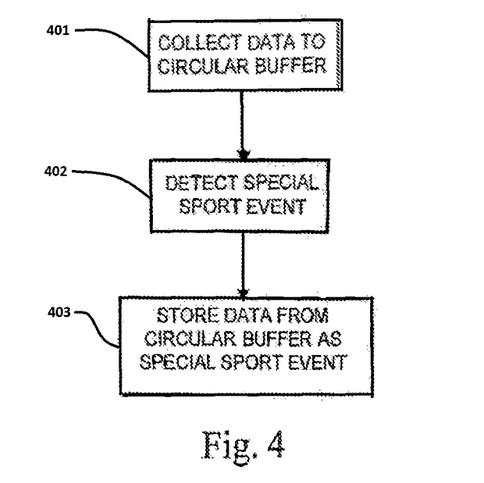

FIG. 4 illustrates a flowchart, wherein the sports watch 1 collects data to a circular buffer memory 20, step 401. The circular buffer memory 20 refers to a data structure that uses a single, fixed-size buffer as if it was connected end-to-end, wherein the data is stored according to the First-In-First-Out principle. With a similar arrangement as in the example of FIG. 3, the data is transmitted to the database of performance data. Within the database, the performance data is categorized and compared with the normal distribution of performances from other sports watch users. If the database detects that, compared to the group, the event is outside the normal range, step 402, the database indicates the sports watch to store data from the circular buffer as a special sport event. The information is saved rather than written over as with regular ring buffer usage. Examples of special events are jogging at unusual hours, a running time considerably faster than the user's average age group, a heart rate lower than others, faster recovery, etc. This function enables the user to highlight remarkable performances automatically or the sports watch may prompt the user to notify an extraordinary performance. It helps the user to record data even after the performance, even if he/she has forgotten to start recording the performance before the exercise. Later the user may browse the performance for example on a desktop computer, wherein special events are already highlighted.

In an embodiment the start time, end time, stating position or the finishing position of the special event is marked in the data stored in the circular buffer memory 20. The data may be transported from the circular buffer memory to the database or to the non-volatile memory of the sports watch 1, wherein the marked data is stored with the circular buffer data. The data stored may be starting from a predetermined period before detecting the special event and/or after detecting the special event. According to various embodiments, the performance data, event data, move data or any chosen period data may be stored in the sports watch and transferred to a computer or a smart phone. The transferred data may be modified with the marked data. For example the start time and position of a running performance may be identified when a change in the speed is detected. Changes in speed may indicate that the runner has stopped walking or has arrived to the location by car. As another example, a hiking event may be marked if the speed of the hiker is detected as being above reasonable limits, such as when the hiker has continued in a car and the speed exceeds 20 km/h. The position information may be detected near a highway generally not allowed for walking, wherein the user of the sports watch 1 may be on a motored vehicle. In an embodiment the sports watch 1 may detect sensor data having a context with automobiles, such as the car position sensor, and mark the detection of the new sensor data. Other examples of detectable car related sensor data that may be used are the engine revcounter, oil pressure, gear, speed, accelerometer or temperature sensor. The event to be detected may be related to motorsports. The detected event data is saved on the sports watch. The performance may be easily limited to the actual performance afterwards as the performance is later viewed on a computer or smart phone. The marked position highlights at least one position or time where the surrounding parameters have changed. This may alleviate the problem where the user has not remembered to start or stop the recording of the sports data at a correct time. The problem could result in distorted performance data; for example, the average speed may calculate actions such as the user driving a car when the recorded event is purposed for running.

In an embodiment of the invention the invention is implemented as computer software that is configured to execute the method and independent features described above when the computer software is executed on a computing device 18. The computer software may be embodied on a computer readable medium or distributed in a network 16 such as the Internet 16. In one example the computer software is executed in the sports watch or in the server 16 from a cloud computing environment 16.

Embodiments of the present invention may be implemented in software, hardware, application logic or a combination of software, hardware and application logic. In an example embodiment, the application logic, software or instruction set is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer or processor 22. A computer-readable medium may comprise a computer-readable storage medium 20 that may be any media or means that can contain or store the instructions for use by or in connection with an instruction execution system, apparatus, or device, such as a computer or processor 22. The exemplary embodiments can store information relating to various processes described herein. This information can be stored in one or more memories 20, such as a hard disk, optical disk, magneto-optical disk, RAM, and the like. One or more databases can store the information used to implement the exemplary embodiments of the present inventions. The databases can be organized using data structures (e.g., records, tables, arrays, fields, graphs, trees, lists, and the like) included in one or more memories or storage devices listed herein. The processes described with respect to the exemplary embodiments can include appropriate data structures for storing data collected and/or generated by the processes of the devices and subsystems of the exemplary embodiments in one or more databases.

All or a portion of the exemplary embodiments can be conveniently implemented using one or more general purpose processors, microprocessors, digital signal processors, micro-controllers, and the like, programmed according to the teachings of the exemplary embodiments of the present inventions, as will be appreciated by those skilled in the computer and/or software art(s). Appropriate software can be readily prepared by programmers of ordinary skill based on the teachings of the exemplary embodiments, as will be appreciated by those skilled in the software art. In addition, the exemplary embodiments can be implemented by the preparation of application-specific integrated circuits or by interconnecting an appropriate network of conventional component circuits, as will be appreciated by those skilled in the electrical art(s). Thus, the exemplary embodiments are not limited to any specific combination of hardware and/or software.

If desired, the different functions discussed herein may be performed in a different order and/or concurrently with each other.

Furthermore, if desired, one or more of the above-described functions may be optional or may be combined. Although various aspects of the invention are set out in the independent claims, other aspects of the invention comprise other combinations of features from the described embodiments and/or the dependent claims with the features of the independent claims, and not solely the combinations explicitly set out in the claims.

It is obvious to a person skilled in the art that with the advancement of technology, the basic idea of the invention may be implemented in various ways. The invention and its embodiments are thus not limited to the examples described above; instead they may vary within the scope of the claims.

What is claimed is:

1. A method for selecting the information displayed on a sports watch including an interface, at least one sensor and a display, the method comprising:
   determining a display mode of the sport watch by a first sensor configured within a housing of the sport watch and by a second sensor which is configured to be wirelessly connected to the interface of the sport watch, the display mode including a plurality of sports modes, each sport mode configured to display sport-specific data on the display;
   detecting a sport event based on movement information received from the first sensor and the second sensor; and
   selecting one of the plurality of sport modes according to the detected sport event, wherein the selection of the one of the plurality of sport modes corresponds to sensor information from the first sensor and the second sensor.

2. The method of claim 1, wherein the interface is a wireless communication interface, wherein the second sensor includes a wireless sensor, and wherein the method further comprises
   receiving wireless sensor information from the wireless sensor via the wireless communication interface;
   comparing the wireless sensor information to predefined reference data, when the wireless sensor information corresponds to the predefined reference data; and
   detecting a sport event based upon the result of the comparison.

3. The method of claim 1, wherein the second sensor comprises at least two wireless sensors and wherein the selection of the sport mode corresponds to sensor information from the at least two wireless sensors.

4. The method of claim 1, further comprising the steps of:
   connecting the sports watch to a database of performance reference data via the interface, wherein the interface comprises a wireless communication interface; and
   receiving the performance reference data from the database.

5. The method of claim 4, further comprising the steps of:
   collecting performance data to a circular buffer;
   comparing the collected performance data to the performance reference data, wherein the performance reference data comprises a typical value range;
   detecting the performance data exceeding the typical value range; and
   storing the performance data as a special sport event.

6. The method of claim 1, further comprising the steps of:
   collecting performance data comprising the movement information for a predefined period;
   comparing the performance data to the performance reference data; and
   storing the performance data in the memory if the collected data is detected as a sport event.

7. A sports watch comprising: a housing;
   a first sensor configured within the housing;
   an interface configured to wirelessly connect to a second sensor;
   wherein one of the sensors is configured to receive movement information;
   a display having at least two display modes, at least one of the display modes being a sport mode configured to display sport-specific data;
   at least one processor; and
   at least one memory containing code to direct the processor and when executed by the processor to cause the sport watch to:
      select the sport-specific data to be displayed on the sports watch,
      detect a sport event based on the movement information received from the first sensor and the second sensor, and
      select the sport mode according to the detected sport event,
      wherein the at least one memory and the computer program code operate together with the at least one processor to cause the sports watch to select the sport mode corresponding to sensor information from the first and the second sensors.

8. The sports watch of claim 7, wherein the second is at least one wireless sensor, wherein the interface is a wireless communication interface for receiving wireless sensor information from the wireless sensor and wherein the memory containing code to further directs the processor to:

receive wireless sensor information from the wireless sensor via the wireless communication interface;

compare the wireless sensor information to predefined reference data, when the wireless sensor information corresponds to the predefined reference data; and further detect the sport event according to the result of the comparison.

9. The sports watch of claim 8, wherein the at least one memory and the computer program code operate together with the at least one processor to cause the sports watch to detect at least two wireless sensors and select the sport mode corresponding to the at least two wireless sensors.

10. The sports watch of claim 8, wherein the at least one memory and the computer program code operate together with the at least one processor to cause the sports watch to connect to a database comprising performance reference data via the wireless communication interface and receive performance reference data from the database.

11. The sports watch of claim 8, wherein the at least one memory and the computer program code operate together with the at least one processor to cause the sports watch to detect the wireless communication interface being connectable to the database of performance references and to receive the performance reference data.

12. The sports watch of claim 8, wherein the at least one memory and the computer program code operate together with the at least one processor to cause the sports watch to:

collect performance data comprising movement information for a predefined period, compare the performance data to the performance reference data, and store the performance data in the memory if the collected data is detected as the sport event.

13. The sports watch of claim 8, wherein the at least one memory and the computer program code operate together with the at least one processor to cause the sports watch to collect performance data to a circular buffer, to compare the collected performance data to the performance reference data, wherein the performance reference data comprises a typical value range, to detect the sport event data exceeding the typical value range and to store the sport event as a special sport event.

* * * * *